(12) United States Patent
Pinho et al.

(10) Patent No.: US 9,247,906 B2
(45) Date of Patent: Feb. 2, 2016

(54) METHOD AND APPARATUS FOR DETECTION OF CATHETER LOCATION FOR INTRAVENOUS ACCESS

(75) Inventors: George P. Pinho, Waterloo (CA); Robert Benjamin Wagner, Kitchener (CA)

(73) Assignee: CHRISTIE DIGITAL SYSTEMS USA, INC., Cypress, CA (US)

(*) Notice: Subject to any disclaimer, the term of this patent is extended or adjusted under 35 U.S.C. 154(b) by 155 days.

(21) Appl. No.: 13/170,498

(22) Filed: Jun. 28, 2011

(65) Prior Publication Data

US 2013/0006178 A1   Jan. 3, 2013

(51) Int. Cl.

| A61B 17/34 | (2006.01) |
|---|---|
| A61M 25/06 | (2006.01) |
| A61M 25/01 | (2006.01) |
| A61B 5/00 | (2006.01) |
| A61B 5/06 | (2006.01) |
| A61M 5/42 | (2006.01) |
| A61B 8/08 | (2006.01) |
| A61B 19/00 | (2006.01) |

(52) U.S. Cl.
CPC .............. *A61B 5/489* (2013.01); *A61B 5/0059* (2013.01); *A61B 5/06* (2013.01); *A61B 8/0841* (2013.01); *A61B 17/3403* (2013.01); *A61B 2019/5293* (2013.01); *A61M 5/427* (2013.01); *A61M 25/0606* (2013.01); *A61M 2025/0166* (2013.01)

(58) Field of Classification Search
CPC .. A61B 5/489; A61B 8/0841; A61B 17/3403; A61B 2019/5293; A61M 5/427; A61M 25/0606; A61M 2025/0166

USPC .............. 600/407, 473, 476; 604/164.01
See application file for complete search history.

(56) References Cited

U.S. PATENT DOCUMENTS

| 4,817,622 A | 4/1989 | Pennypacker et al. |
|---|---|---|
| 5,519,208 A | 5/1996 | Esparza et al. |
| 5,608,210 A | 3/1997 | Esparza et al. |
| 6,178,340 B1 | 1/2001 | Svetliza |
| 7,239,909 B2 | 7/2007 | Zeman |
| 7,930,014 B2 | 4/2011 | Huennekens et al. |
| 2004/0019280 A1 | 1/2004 | Waner et al. |
| 2006/0036164 A1 | 2/2006 | Wilson et al. |
| 2006/0036167 A1 | 2/2006 | Shina |

(Continued)

FOREIGN PATENT DOCUMENTS

| CN | 1117707 A | 2/1996 |
|---|---|---|
| CN | 1602168 A | 3/2005 |

(Continued)

OTHER PUBLICATIONS

Corresponding European Patent Application No. 12153024.0 Search Report dated Sep. 24, 2012.

(Continued)

*Primary Examiner* — Nathan R Price
(74) *Attorney, Agent, or Firm* — Perry + Currier, Inc.

(57) ABSTRACT

A system is set forth for detection of catheter location for intravenous access, comprising a catheter having a light source for illuminating a needle tip thereof; and an infrared detector and image projector for simultaneously detecting image vasculature and the location of the needle tip below the surface of the skin and in response projecting an image onto the skin to reveal the location of the needle tip relative to the vasculature.

24 Claims, 7 Drawing Sheets

(56) References Cited

U.S. PATENT DOCUMENTS

| | | |
|---|---|---|
| 2006/0122515 A1 | 6/2006 | Zeman et al. |
| 2006/0173351 A1* | 8/2006 | Marcotte et al. ............. 600/473 |
| 2007/0158569 A1 | 7/2007 | Zeman |
| 2008/0039715 A1 | 2/2008 | Wilson et al. |
| 2008/0194930 A1 | 8/2008 | Harris et al. |
| 2010/0051808 A1 | 3/2010 | Zeman et al. |
| 2010/0094126 A1 | 4/2010 | Imam |
| 2011/0009738 A1 | 1/2011 | Zemel |
| 2011/0125028 A1 | 5/2011 | Wood et al. |

FOREIGN PATENT DOCUMENTS

| | | |
|---|---|---|
| CN | 201469867 U | 5/2010 |
| JP | 2004-237051 A | 8/2004 |
| WO | 94/17732 A1 | 8/1994 |
| WO | 02/103409 A2 | 12/2002 |

OTHER PUBLICATIONS

Corresponding Chinese Patent Application No. 201210060954.2, "First Office Action—with English Translation" dated Dec. 2, 2014.

\* cited by examiner

METHOD AND APPARATUS FOR DETECTION OF CATHETER LOCATION FOR INTRAVENOUS ACCESS

BACKGROUND OF THE INVENTION

1. Field of the Invention

The present invention is directed to medical imaging and more particularly to a method and apparatus for detection of catheter location for intravenous access.

2. Description of the Related Art

Intravenous (IV) catheters are used to access veins for blood draw, and for fluid delivery. There are very few techniques for assisting nurses and clinicians in verifying a positive cannulation of a vein. The standard technique for peripheral IV access involves using a tourniquet to engorge veins, followed by palpation to identify a suitable vein and finally insertion of the catheter needle. Clinicians must rely on "feel" when inserting the needle into a vein and on observing blood flashback to ascertain when the catheter has successfully cannulated the vein. Statistics indicate that this trial-and-error process requires an average of 2.4 attempts and up to 20 min for a clinician to successfully cannulate a vein. Aside from the increased pain and anxiety experienced by patients, there are real costs associated with IV care. Patient throughput, nurse time, consumables, and increased infection rates all contribute to increased medical care costs for hospitals and governments.

Systems have been developed for assisting in venous access and which overcome the disadvantages of the traditional trial-and-error procedure discussed above. One such system is the VeinViewer® infrared detector and image projector manufactured and sold by Christie Medical Holdings, Inc., a division of Christie Digital Systems, Inc., which is described in U.S. Pat. No. 7,239,909, and US Publication Nos. 2010051808, 20070158569 and 20060122515, the contents of which are incorporated herein by reference.

According to the VeinViewer® system, diffuse infrared light is used to image vasculature below the surface of the skin, and the image is then projected onto the skin to reveal the location of the vasculature. The vasculature image is projected in exactly the same anatomical location as the vasculature itself, and in its three-dimensional context (skin of patient) making it very easy to see the vessels. Also, since there is no transducer to hold, the clinician's hands are free to deal with venous access.

Although the VeinViewer® system has been widely adopted by hospitals, its application has been somewhat limited by the fact that it cannot detect a successful cannulation event. For this, ultrasound is the only current visualization technology that can show if a successful cannulation has occurred. Ultrasound is commonly used for deep vein access such as PICC lines and CVC's, but is not typically used for peripheral veins.

Examples of ultrasound imaging systems for acquiring images of the vasculature include US Publication No. 20060036167 which discloses a system for acquiring angiographic images and locating a catheter within a blood vessel, and U.S. Pat. No. 7,930,014 which discloses a system for locating a catheter inside a body and the simultaneous display of two images: an angiographic representation of the location of the catheter and an image captured by the catheter.

Additional prior art of interest is as follows: US Publication Nos. 20080194930; 20100094126; 20080039715; 20060036164; 20110009738 and U.S. Pat. Nos. 6,178,340; 5,519,208; 5,608,210 and 4,817,622.

US Publication No. 20080194930 discloses modifying a catheter needle surface to facilitate detection of the needle by an IR camera.

US Publication No. 20100094126 discloses the use of an optical fibre to locate the tip of the needle by extending the fibre out the end of the needle, and the use of absorbed and re-emitted light to find a vein. The application envisions a clinician passing the needle over the skin to detect the presence of a vein beneath and watching for a corresponding change in optical return. There is no imaging of the needle or the vein.

U.S. Pat. No. 6,178,340 discloses an infrared imaging system for detection of veins near the surface of a patient's skin. A screen is used to show the clinician where the veins are located. There is no imaging of the catheter/needle.

U.S. Pat. No. 5,519,208 discloses the use of a near infrared LED to mark the tip of the needle/catheter. The image of the needle/catheter is seen through a screen or via a mirror that enables viewing of the image and the patient simultaneously.

U.S. Pat. No. 5,608,210 also discloses the use of a near infrared LED to mark the tip of the needle/catheter. The image of the needle/catheter is seen through special headgear worn by the clinician. The head-mounted instruments are intended to overcome the problem of viewing a monitor while attempting to cannulate a vein.

U.S. Pat. No. 4,817,622 discloses the use of a fibre to illuminate tissue.

US Publication Nos. 20080039715 and 20060036164 disclose the use of a light emitting tip to locate a catheter within a patient and the use of pulsed light signals to facilitate such detection. The pulsed signals are meant to facilitate locating the catheter by giving instruments a known signal type, e.g. rhythmic pulses, to detect and track within the body.

US Publication No. 20110009738 discloses the use of changes in the surface properties of the needle to facilitate tracking by an IR camera as well as the use of the properties of blood to modify the signal received by the IR camera in order to detect a successful cannulation.

It is an object of an aspect of this specification to set forth a system for detecting the position of a catheter using infrared based imaging but which eliminates the prior art difficulties in detecting a positive cannulation.

SUMMARY OF THE INVENTION

It is an aspect of the present invention to provide a system for detecting cannulation of a catheter, comprising a needle, a light source, a camera and a projector. The light source illuminates a patient's skin in an area of interest. The light is reflected and scattered by tissue but absorbed by hemoglobin in the blood. The camera detects the reflected light and the projector then projects the image obtained by the camera onto the patient's skin thereby providing a map of the patient's blood vessels that is visible to the clinician. The needle is made detectable by projecting light from its tip. This can be accomplished by threading a fibre through the needle to a position at or near the tip or by using the hollow needle itself as a light guide. The light illuminates the tissue surrounding the vein but is absorbed by hemoglobin in the blood. Therefore, as the needle is pushed into the patient's skin the tip will continue to be visible to the camera until a successful cannulation event has occurred, indicated by the light emitted from the tip of the needle being absorbed by the hemoglobin in the blood resulting in a substantial decrease in the light being detected by the camera. An image of the needle may also be projected onto the patient's skin to aid the clinician in positioning the needle. This can be accomplished using two different wavelengths of light for illuminating the skin and the needle tip or by alternating pulses of light for alternately illuminating the skin and the needle tip.

These together with other aspects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENTS

Figure 1:
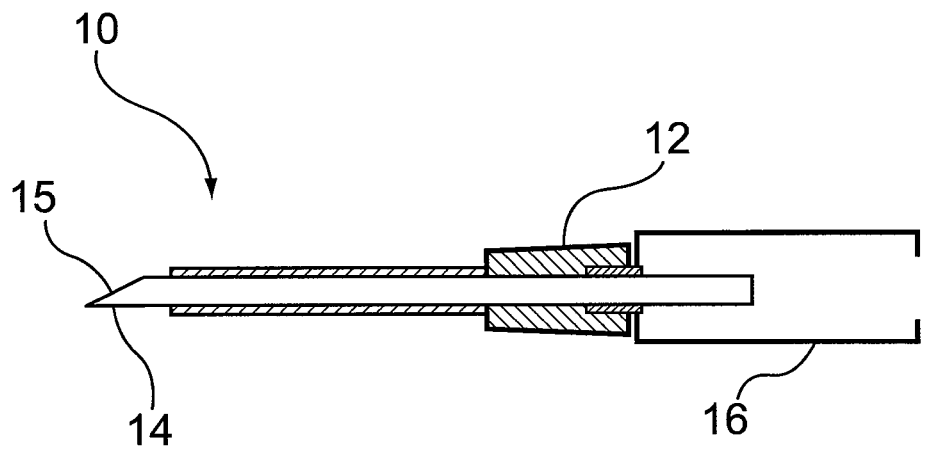
FIG. 1 is a cross-section view through a conventional IV catheter, according to the prior art.

A conventional prior art catheter 10 for peripheral IV access is shown in FIG. 1, including a catheter housing 12 sheathed over an introducer needle 14, which terminates in a needle housing 16. The introducer needle 14 is used to insert the catheter into a vein. Once the vein is cannulated, the introducer needle 14 is removed leaving the catheter 10 in place.

Figure 2:
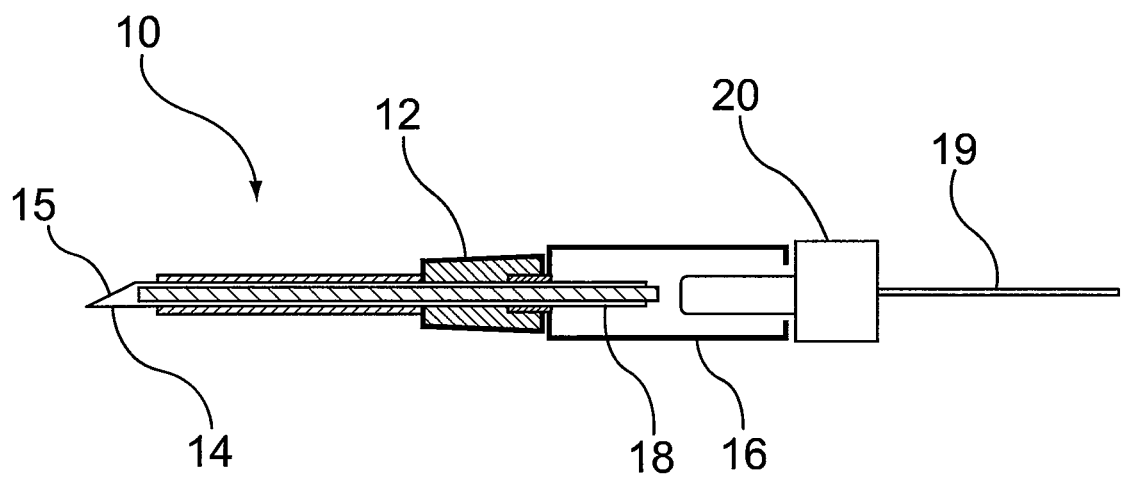
FIG. 2 is a cross-section view through an IV catheter with light source for detection of catheter location, according to a first embodiment.

According to a first embodiment, as shown in FIG. 2, the IV catheter 10 of FIG. 1 can be illuminated via a fibre optic light guide 18 disposed within the needle 14. The light guide is illuminated from the needle housing 16 and propagates light to the needle tip 15. A source of illumination or illuminator (discussed in greater detail with reference to FIGS. 6 and 7) generates light at a wavelength chosen to be transparent to tissue but readily absorbed by haemoglobin. Wavelengths in the range of 650-1100 nm are suitable. The illuminator can be a laser, LED or other suitable light source, and can be disposed within housing 16 or can be connected to the housing from a remote location via optical fibre 19 and a light source coupler 20. The coupler 20 ensures accurate alignment between the light-generating tip of the optical fibre 19 and the light guide 18. The use of a remote illuminator also eliminates any obtrusion around the catheter, for ease of insertion.

Figure 3:
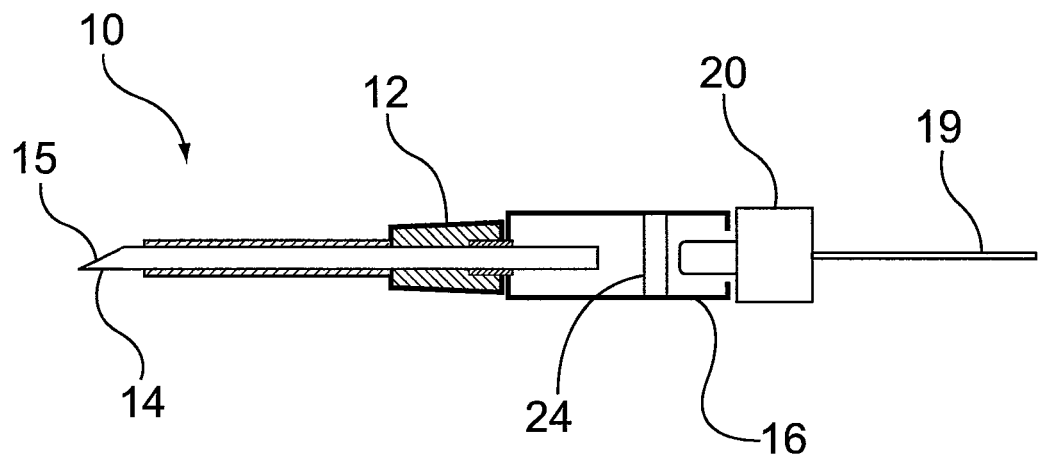
FIG. 3 is a cross-section view through an IV catheter with light source for detection of catheter location, according to a second embodiment.

In a second embodiment, shown in FIG. 3, the hollow needle 14 is used as a light guide such that no fibre 18 is required. The light source coupler 20 mounts directly to the needle housing 16 and self-aligns with the back of the needle 14. Light propagates down the needle shaft and is reflected out at the sharp side of the needle 14.

A window 24 is molded into the plastic needle housing 16. The purpose of the window 24 is to create a blood flashback chamber that can be used as a visual detector for cannulation while preventing blood from contaminating the light source coupler 20.

Figure 4:
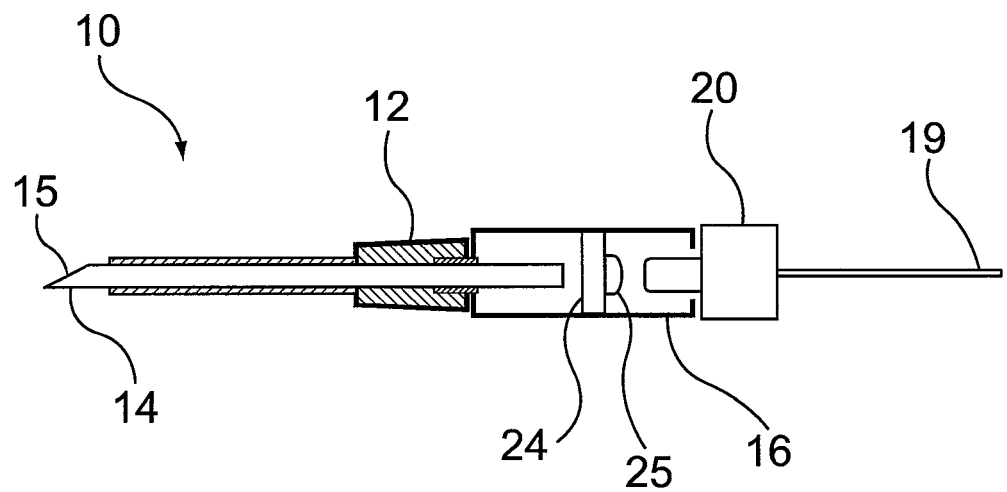
FIG. 4 is a cross-section view through an IV catheter with light source for detection of catheter location, according to a third embodiment.

In a third embodiment, illustrated in FIG. 4, a plano-convex lens 25 is provided having a suitable radius to match the fibre numerical aperture output of optical fibre 19 for enhanced optical coupling into the needle 14. The lens 25 can be molded into the optical window 24 as part of the manufacturing process. The lens 25 focuses the diverging light emitted from the optical fibre 19 to a point at the opening in the end of the needle 14. This ensures maximum light coupling and light transmission to the needle tip 15.

Figure 5:
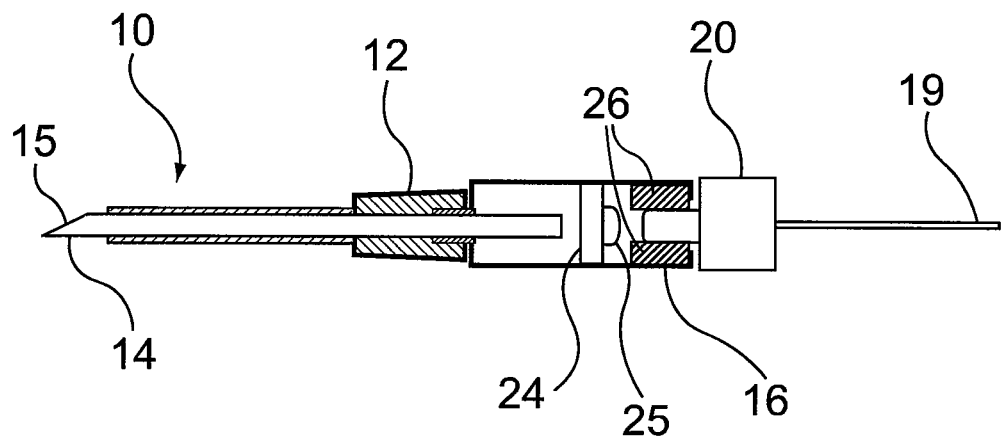
FIG. 5 is a cross-section view through an IV catheter with light source for detection of catheter location, according to a further embodiment.

According to a further embodiment, illustrated in FIG. 5, a self-centering mechanism 26 is provided in the walls of the needle housing 16 to ensure the light source coupler 20 self centers to the optical window 24 and lens 25. This can be accomplished using a slight taper to the needle housing walls that matches the light source coupler. In this way, the coupler self centers but can also be "locked" in place by friction. Alternatively, a quarter-turn thread (not shown) can also be used to attach the light coupler 20. In this case, a matching thread (not shown) is placed on the needle housing 16 to engage the light coupler 20.

Figure 6:
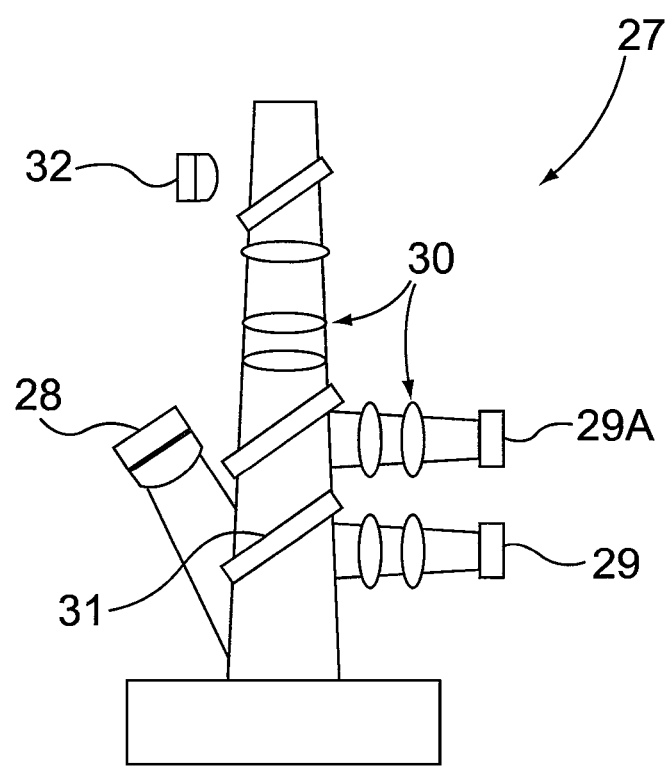
FIG. 6 is a schematic representation of an IR imager and projector forming part of an exemplary embodiment of a system for detection of catheter location for intravenous access.

FIG. 6 is a schematic representation of a modified version of a VeinViewer® infrared detector and image projector 27 manufactured and sold by Christie Medical Holdings, Inc., as discussed above, for incorporation into the system of FIG. 7, discussed in greater detail below. The infrared detector and image projector 27 is described in detail in the patents and patent applications referred to above. In general, infrared detector and image projector 27 comprises an IR illuminator 28, an IR imager 29, image processing circuitry and imaging optics 30 and a projector 32. The IR light illuminates a patient's tissue with light in the range of 650-1100 nm, which is absorbed by haemoglobin. The unabsorbed light is reflected back and is detected by the IR imager 29. The reflected image is processed by image processing circuitry and imaging optics 30, and then re-projected back in real-time via the projector 32 to show the location of blood vessels beneath the patient's skin. The IR imager 29 includes a cut-off filter to differentiate reflected imaging light from background IR light in the environment.

In addition to the IR illuminator 28, an additional IR illuminator 28A, may be provided for illuminating the IV catheter 10, and a second IR imager 29A and optical separator 31 may be provided for detecting light reflected from illuminator 28A. The modified system of FIG. 6 may be combined with the IV catheter 10 of any one of FIG. 2 or 5, to create a system for detection of catheter location for intravenous access, as shown in FIG. 7.

Figure 7:
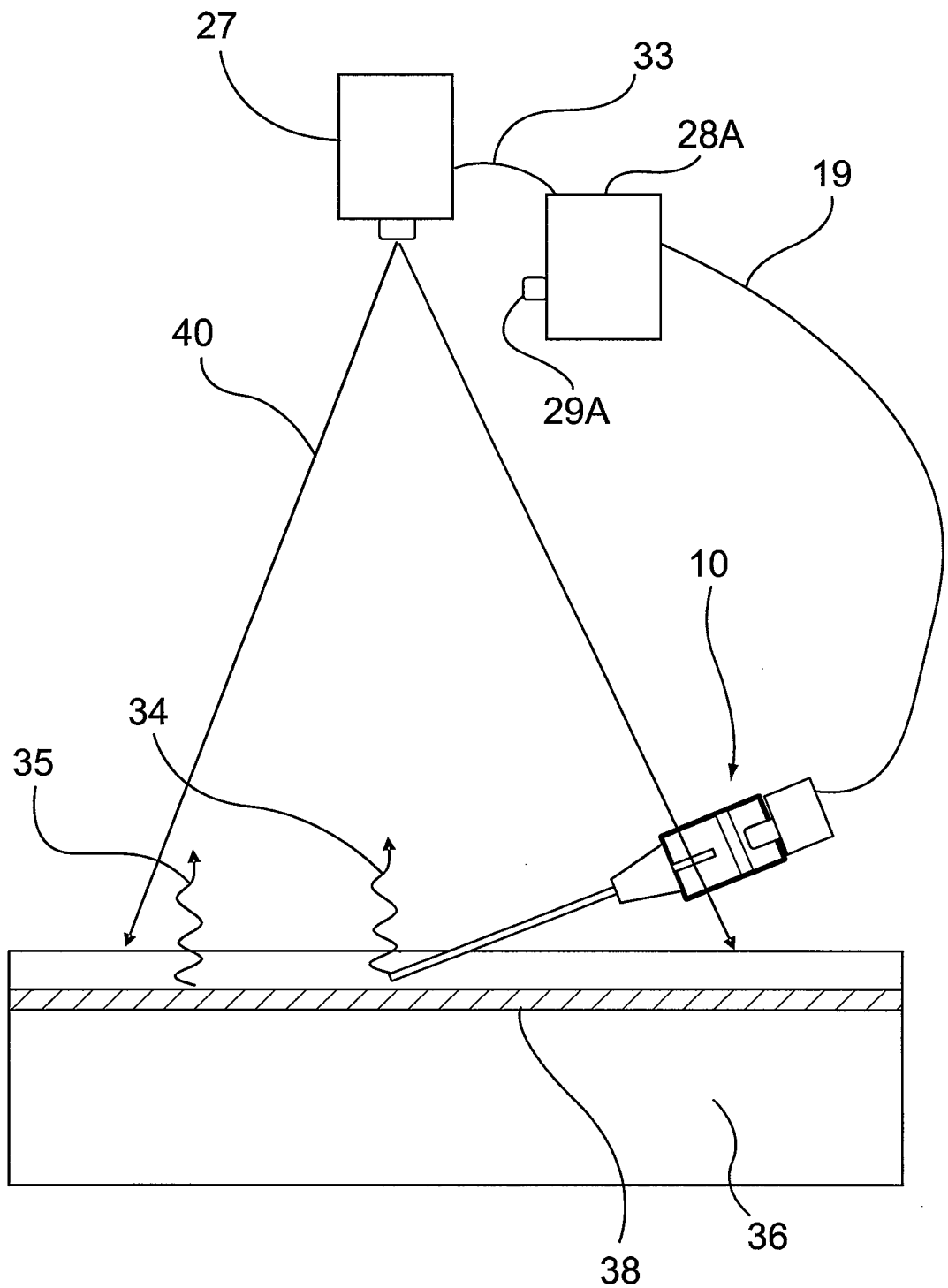
FIG. 7 is a schematic representation of a system for detection of catheter location for intravenous access, incorporating the catheter of FIGS. 2-5 and the IR imager and projector of FIG. 6, according to a further embodiment.
Figure 8A:
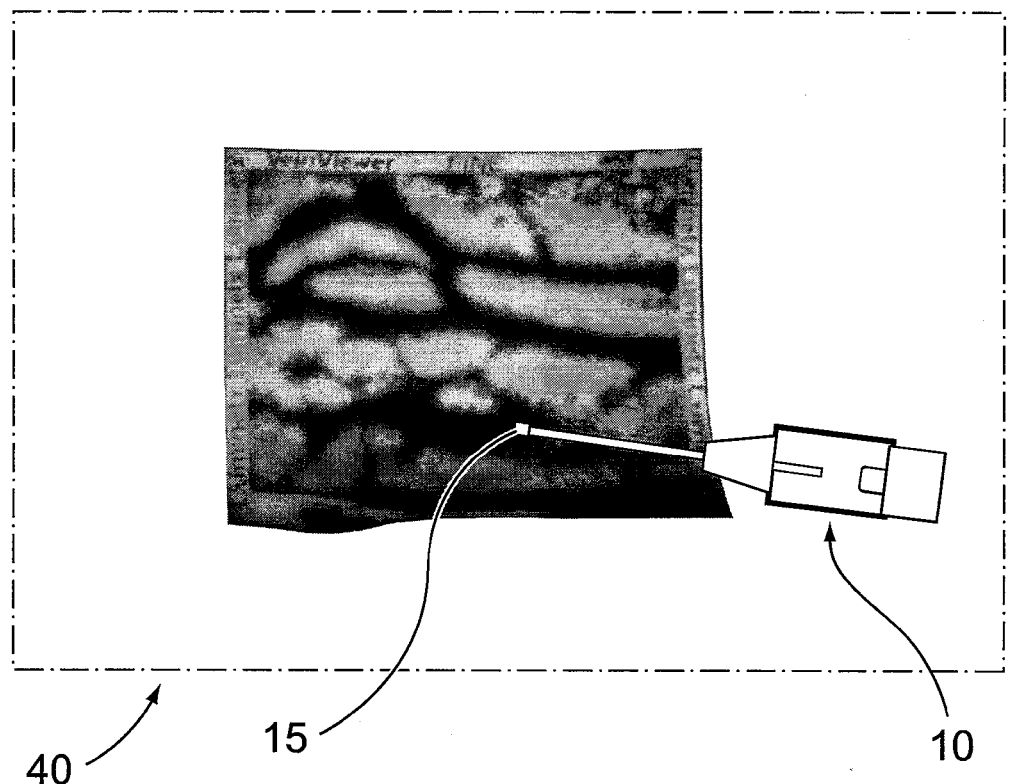
FIGS. 8A, 8B and 8C show images projected onto the arm of a patient using the system of FIG. 7.
Figure 8B:
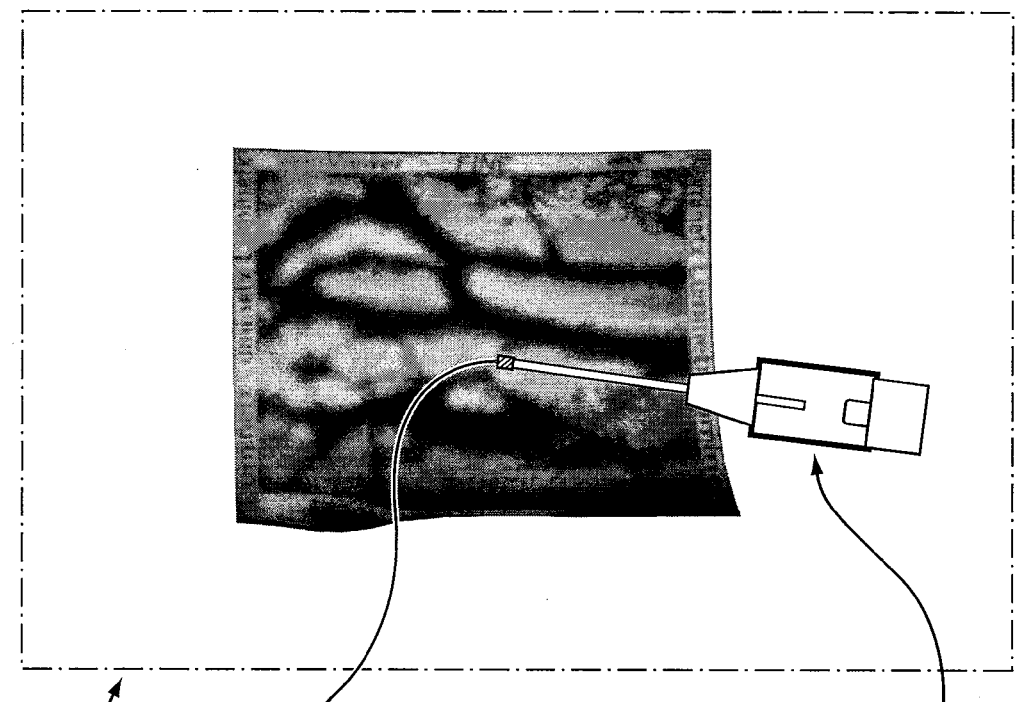
Figure 8C:
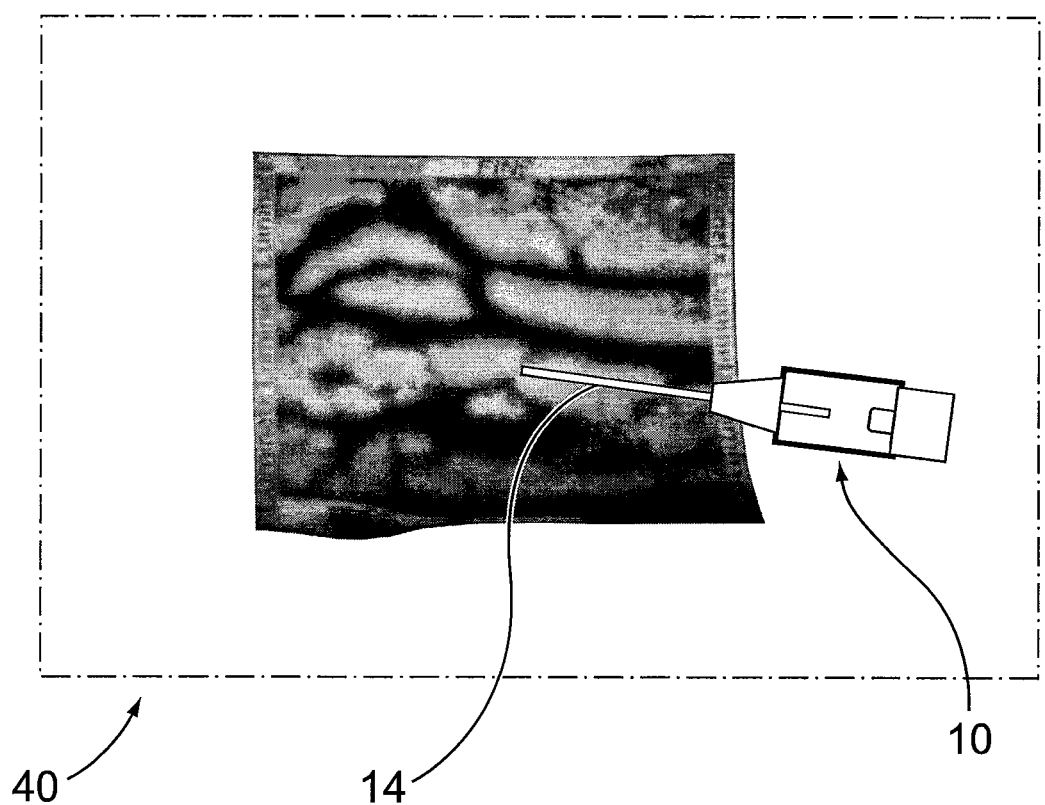

In the system of FIG. 7, the infrared detector and image projector 27 is connected to additional IR illuminator 28A via a USB cable 33, which illuminates the IV catheter 10 via optical fibre 19 and light source coupler 20 (FIGS. 2-5). The wavelength of illumination of this additional light source is also in the range of 650-1100 nm but at a second wavelength that is different than the first wavelength output from the IR illuminator 28, and is preferably separated from the first wavelength by at least 50 nm. Light 34 emanating from the tip 15 of the catheter is filtered by optical separator 31 and detected by the IR imager 29A. Light 35 from illuminator 28 that has not been absorbed by haemoglobin is reflected by the tissue and detected by the IR imager 29 whereas light absorbed by haemoglobin results in an absence of reflected light 35 indicative of vein 38. Imagers 29 and 29A therefore detect both the image of the veins and the image of the catheter simultaneously. Both detectors are preferably identical in aspect ratio and resolution to ensure proper image alignment between the two images. The catheter housing 16 is also detectable by the IR imager 29A for orienting the axis of the needle in space. With the tip 15 of the needle and the housing detected, the infrared detector and image projector 27 can project an image 40 onto the surface of the skin showing the location of the needle 14 relative to the tissue 36 and vein 38 in the image map, for example by illuminating the IV catheter 10 in a different color from the rest of the image, as shown in FIGS. 8A-8C.

As the needle is pushed into the skin, the illuminated tip 15 continues to be detected by the IR imager 29A of infrared detector and image projector 27 since the chosen wavelength is not readily absorbed by tissue. The infrared detector and image projector 27 maintains a projection of the entire needle so that the clinician has a visual reference of the needle position relative to the vein 38. Once the needle penetrates the vein, blood flashes back through the needle, as described above. Since blood is a good absorber of wavelengths in the range of 650-1000 nm, the light emanating from the needle tip 15 diminishes substantially. As the light diminishes, the IR imager 29A eventually detects a condition wherein no light is detected. This condition is fed back to the image processing circuitry which in response changes the color on the needle projection to indicate to the clinician that the needle has entered the bloodstream. Additional information can also be added via text on the image to indicate to the operator that the blood vessel is cannulated.

Wavelength separation can also be detected using a single IR imager 29 in at least one other way. The first and second wavelengths can be separated using a mirror composed of two equal sized band-pass filters (not shown). The first filter reflects the primary wavelength onto one half of imager 29 and allows transmission of the second wavelength. The second filter reflects the secondary wavelength onto the other half of imager 29 and transmits the primary wavelength. With suitable imaging optics in front of the imager 29, each wavelength may be focussed onto one half of the imager. The two imaging halves are partitioned to be identical in aspect ratio and resolution. The acquired images of either the veins or the catheter can then be processed and overlaid in the projected image to locate the catheter position.

According to a further embodiment, light pulse modulation may be used to illuminate the catheter 10 but at the same wavelength of light as generated by the IR illuminator 28. This removes the need for an additional imager ay the second wavelength and simplifies the design of the imaging optics 30 required to resolve different wavelengths. In this embodiment, the imager 29 acquires images at a speed of between 20-30 frames per second. Preferably, this speed is maintained in duplex, which means alternating images of the vein pattern and needle are acquired at a rate of 40-60 frames per second. However, this higher acquisition speed reduces the amount of light impinging on the imager and thus reduces signal/noise ratio. In order to compensate for this, pixel binning can be employed to reduce the resolution while improving the signal/noise ratio. If adequate signal/noise ratio cannot be achieved at 40-60 frames per second then a lower frame rate of 20-30 frames per second can be used, although this will introduce visible lag into the projected image.

Using timed light pulsing, the image of the vein map and catheter are separated by sequentially pulsing the IR illuminator 28 and the IR illuminator 28A for the IV catheter 10 so that the IR imager 29 sees only one of either the vein image or the IV catheter image at any point in time. By using pulse modulation, the infrared imager 29 and image projector 27 can operate at the same wavelength for the vein image and the catheter image.

For this embodiment, the timing between the light pulses from IR illuminator 28, the needle-tip IR illuminator 28A, and the imager 29 is synchronized such that the imager 29 is virtually shuttered to only acquire scattered or transmitted light from one of either the illuminator 28 or illuminator 28A in sequential frames. Frame synchronization can be achieved in one of two ways.

First, electronic synchronization may be provided by a microcontroller within the infrared detector and image projector 27 which communicates with and configures both IR illuminator 28 and IR imager 29. The imager 29 is caused to capture sequential frames as follows: A, B, A, B, etc., where A=vein image and B=catheter, with virtual shuttering of the imager 29 between frames. This sequencing is used to cause the IR illuminator 28 to illuminate during frame capture A and to turn off during frame capture B. A sync signal can also be output over the USB cable 33 so as to cause illuminator 28A to illuminate the external needle tip 15 during frame capture B and be turned off during frame capture A.

Second, optical synchronization may be provided using the same synchronization pattern as set forth above, but using an optical signal. In this case, the needle-tip illuminator 28A is disposed in close proximity to the infrared detector and image projector 27, such that when the illuminator 28 is turned on (frame capture A), the IR imager 29 detects this light and trips a switch to turn off the needle-tip illuminator 28A.

A final and simpler method to differentiate light received from illuminators 28 and 28A is to use intensity filtering. Instead of using two IR imagers 29 and 29A for detecting reflected light projected onto the patient by the illuminators 28 and 28A at different wavelengths, a single IR imager 29 can be used to detect reflected light projected onto the patient by the illuminators 28 and 28A at the same wavelength but at different amplitudes or intensities. Light from illuminator 28A can be made brighter than light from illuminator 28, which is detected by IR imager 29 and re-projected back on to the patient's skin via projector 32 with the catheter needle being distinguishable by its higher brightness. The light from the needle tip 15 is much brighter and more concentrated than the diffuse scattered light that is back-scattered from the bulk tissue around veins. This difference in relative brightness can be used by image processing software and circuitry and grey scale filtering to allow the catheter housing 16 and needle 14 to be discerned from the background vein image. However, this technique reduces the overall dynamic range of the imaging system.

FIGS. 8A-8C show vein map images acquired using the system of FIG. 7, with images of the catheter 10 with the illuminated catheter tip 15 indicated using coloured projection. Thus, in FIG. 8A, the tip 15 may be shown in a first colour (e.g. red) prior to cannulation while FIG. 8B shows the tip 15 in a second colour (e.g. yellow) to indicate that vein cannulation has been achieved, and in FIG. 8C the catheter needle 14 is shown beneath the surface of the skin via a coloured line (e.g. yellow) for indicating orientation of the catheter in space.

The present invention has been described with respect to the forgoing embodiments and variations. Other embodiments and variations are possible. For example, instead of including a window 24, as in FIG. 3, an optical plug can be placed at the end of the needle to prevent blood flashback from contaminating the light source coupler 20. The optical plug can, for example, be a clear medically approved plastic window that is placed on the end of the needle 14 to allow light transmission down the hollow needle.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the claims.

What is claimed is:

1. A system for detection of a needle tip of an introducer needle during cannulation of a catheter, said catheter having a catheter housing sheathed over an introducer needle, comprising:
   an illuminator for illuminating said needle tip of said introducer needle; and
   an infrared detector and image projector for simultaneously detecting vasculature and illumination of said needle tip below skin surface and in response projecting an image of said vasculature and needle tip onto the skin surface to reveal the location of said needle tip relative to said vasculature,
further including a light guide disposed within said introducer needle and terminating at said needle tip, wherein said illuminator illuminates said light guide so as to propagate light through the light guide for projection from said needle tip.

2. The system of claim 1, wherein said illuminator generates light at a wavelength that is transparent to tissue but readily absorbed by haemoglobin.

3. The system of claim 2, wherein said wavelength is in the range of 650-1100 nm.

4. The system of claim 3, wherein said illuminator is a laser.

5. The system of claim 3, wherein said illuminator is an LED.

6. The system of claim 1, wherein said illuminator is disposed within a housing at an end of said catheter remote from said needle tip.

7. The system of claim 1, further comprising a light source coupler for providing alignment between the illuminator and said light guide.

8. The system of claim 1, wherein light from said illuminator is directed through said needle to said tip.

9. The system of claim 8, wherein said catheter is connected to an optical fibre that is coupled to a needle housing via a light source coupler, said housing being disposed at an end of said catheter remote from said needle tip, wherein said coupler provides alignment between the optical fibre and said light guide such that light is directed through said needle to said tip.

10. The system of claim 9, wherein said catheter further comprises a clear medically-approved plastic window that is moulded into said needle housing to create a blood flashback chamber for use as a visual indicator of cannulation.

11. The system of claim 10, further comprising a plano-convex lens molded into said window and having a radius that matches the fibre numerical aperture output of said optical fibre for optical coupling of said light into the needle.

12. The system of claim 11, wherein said illuminator generates light at a wavelength that is transparent to tissue but readily absorbed by haemoglobin.

13. The system of claim 11, wherein said wavelength is in the range of 650-1100 nm.

14. The system of claim 11, wherein said illuminator is a laser.

15. The system of claim 11, wherein said illuminator is an LED.

16. The system of claim 1, wherein said infrared detector and image projector includes a first illuminator for illuminating said vasculature, a second illuminator for illuminating said catheter, a first IR imager for detecting reflected light that has not been absorbed by haemoglobin, and a second IR imager for detecting light from said needle tip and light reflected from said catheter.

17. The system of claim 16, wherein the wavelengths of illumination of said first and illuminators are each in the range of 650-1000 nm but are at different wavelengths and are separated from each other by at least 50 nm.

18. The system of claim 1, wherein said infrared detector and image projector includes a first illuminator for illuminating said vasculature, a second illuminator for illuminating said catheter, and an IR imager for detecting reflected light that has not been absorbed by haemoglobin as well as light from said needle tip and light reflected from said catheter, wherein said first illuminator is modulated to generate timed light pulses, and said second illuminator is modulated to generate timed light pulses at times when said first illuminator is not generating light pulses.

19. The system of claim 18, wherein said second illuminator is disposed in close proximity to said IR imager such when the first illuminator is turned on the IR imager detects the light therefrom and causes said second illuminator to turn off.

20. The system of claim 1, wherein said infrared detector and image projector includes a first illuminator for illuminating said vasculature, a second illuminator for illuminating said catheter, and an IR imager for detecting reflected light that has not been absorbed by haemoglobin as well as light from said needle tip and light reflected from said catheter, wherein light from the second illuminator is brighter than light from the first illuminator, such that the IR imager distinguishes between bright light from the second illuminator and reflected diffuse light from the first illuminator that has not been absorbed by haemoglobin.

21. The system of claim 20, wherein said IR illuminator distinguishes between said bright light and reflected light using image processing and grey scale filtering.

22. The system of claim 1, wherein said image is projected onto the skin using coloured projection to reveal the location of said needle relative to said vasculature.

23. The system of claim 1, wherein said light guide is an optical fibre.

24. The system of claim 1, wherein said light guide comprises a shaft of said introducer needle.

\* \* \* \* \*